United States Patent [19]

Balogh et al.

[11] Patent Number: 4,843,174

[45] Date of Patent: Jun. 27, 1989

[54] PROCESS FOR SEPARATING PYETHROID GEOMETRIC ISOMERS

[75] Inventors: Gyula Balogh, Budapest; Iren Boros neée Gundar, Budaórs; Antal Gajáry; György Hidasi, both of Budapest; András Rappi, Érd; József Rákóczi, Budapest; Rudolf Soós, Budapest; Istvan Székely, Dunakeszi; Sandor Zoltan, Budapest, all of Hungary

[73] Assignee: Chinoin Gyogyszer Es Vegyeszeti Temekek Gyara Rt, Budapest, Hungary

[21] Appl. No.: 902,460

[22] PCT Filed: Dec. 6, 1985

[86] PCT No.: PCT/HU85/00072

§ 371 Date: Sep. 26, 1986

§ 102(e) Date: Sep. 26, 1986

[87] PCT Pub. No.: WO86/03487

PCT Pub. Date: Jun. 19, 1986

[51] Int. Cl.$^4$ .............................................. C07C 51/43
[52] U.S. Cl. .................................................. 562/506
[58] Field of Search ................................. 562/401, 506

[56] References Cited

U.S. PATENT DOCUMENTS 3,666,798  5/1972  Matsui ................................. 562/401
4,236,026 11/1980  Naumann ............................ 562/401
4,306,077 12/1981  Leigh .................................. 562/401
4,337,352  6/1982  Naumann ............................ 562/401
4,599,444  7/1986  Foggussy ............................ 562/401
4,683,089  7/1987  Leigh .................................. 562/401

FOREIGN PATENT DOCUMENTS 0003060  7/1979  European Pat. Off. .
0006187  1/1980  .
0119463  9/1984  European Pat. Off. .
2043173  4/1971  Fed. Rep. of Germany .
2035308  8/1980  United Kingdom .

Primary Examiner—Michael L. Shippen
Attorney, Agent, or Firm—Herbert Dubno

[57] ABSTRACT

The invention relates to the separation of the geometrical isomers of cyclopropane carboxylic acids of formula (I)

wherein R represents alkyl having 1 to 4 carbon atoms or halogen.

5 Claims, No Drawings

PROCESS FOR SEPARATING PYETHROID GEOMETRIC ISOMERS

The invention relates to the separation of the geometrical isomers of cyclopropane carboxylic acids of formula (I)

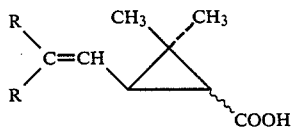

wherein
R represents alkyl having 1 to 4 carbon atoms or halogen.

The separated geometrical isomers compared with the isomeric mixtures may be used as starting materials of novel pyrethroids having very favorable insecticidal properties.

It is known that many of the insecticidal pyrethroids, which have a substituted cyclopropane carboxylic acid skeleton, are the mixtures of geometrical and optical isomers. In recent decades much search and development has been directed to the more effective isomers and to their preparation, respectively, since a relation between the structure and the effectiveness has been found. The greater effectiveness relates not only to the greater biological activity but also to superior toxicological, environmental and optionally economical considerations.

The isomeric ratio of the synthetic, substituted cyclopropane was adjusted to the advantageous value in many ways. E.g. in the most usual synthesis of the cyclopropane ring formation (cycloaddition) the methylene transfer catalysts were varied. First of all copper and copper compounds (J. Am. Chem. Soc., 74, 5376 (1952); J. Am. Chem. Soc. 73, 5301, [1951]; Chem. Ber. 99, 2855 [1966]; Bull. Chem. Soc. Jap. 40, 2392 [1967]), organic metal complexes (Chem. Com. p. 1378 [1968]; J. Org. Chem. 16, p. 30 [1969]; J. Org. Chem. 23, p. 215 [1970]; Chem. Com. p. 1199 [1967]; Che. Com. p. 1220 [1970], J. Org. Chem. 22, C 39 [1970] were used. In case of the formation of the substituted base skeleton the mass production of the desired favorable isomers is not, however, a feasable way from an industrial, technological and economical point of view and this is also valid for the cyclopropane carboxylic acid derivatives (GB-PS 1,446,304, J. Org. Chem. 17, 381 [1952], GB-PS 1,413,491).

For the separation of the stereoisomeric (cis, trans) mixtures of substituted cyclopropane carboxylic acids the fractionated crystallization is suggested most widely in the literature (Coll. Czech. Chem. Com. 24, 2230 [1959]; Pestic. Sci. 1974, 532; Pestic, Sci. 1974, 791).

The efficiency and economy of these processes is generally not satisfactory.

The separations on the basis of solvent selectivity are also not suitable. According to these processes e.g. in case of chrysanthemic acid and permethrinic acid medium yields are obtained. Furthermore great amounts of benzene or petrolether are used for the recrystallization or digeration is performed (Coll. Czech. Chem. Com. 24, 2230 [1959]). The same may be stated for other processes based on solvent selectivity (Pestic. Sci. 1971, 245; DE-OS No. 2,439,177).

A new and witty solution is described (DE-PS No. 2,800,922) according to which two moles of cyclopropane carboxylic acid sodium salt are reacted with one mole of racemic alpha-phenylethylamine whereafter the phenylethylamine salt of the cis isomer may be separated from the sodium salt of the trans isomer. After extraction with ether from the aqueous phase the isomeric purity is, however, only 80/20 and 20/80, respectively. The disadvantage of this process is also that higher isomeric purity may be obtained by recrystallization from petrolether. This means a fractionated recrystallization with a 60% conversion calculated from the material balance.

The invention is based on the recognition that the geometrical isomers of the cyclopropane carboxylic acids of formula (I)

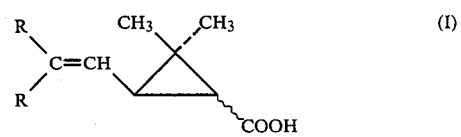

may be separated with great selectivity through their salts of formula (IV)

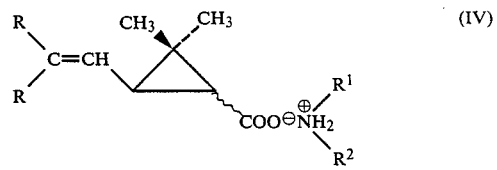

formed with the compounds of formula (II)

in a suitable buffered aqueous medium.

The invention is characterized by
(a) treating a cyclopropane carboxylic acid of formula (I)

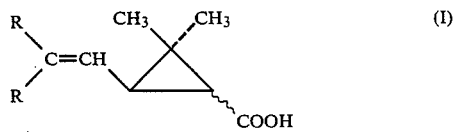

wherein
R represents alkyl having 1 to 4 carbon atoms or halogen with a compound of formula (II)

wherein
$R^1$ and $R^2$ are independently hydrogen, straight or branched chained alkyl having 1 to 5 carbon atoms, straight or branched chained alkenyl having 2 to 5 carbon atoms, phenyl, aralkyl having 7 to 9 carbon atoms, or $R^1$ and $R^2$ together form a nitrogen or oxygen containing heterocyclic group containing 4 or 5 carbon atoms, to form
a part of formula (IV)

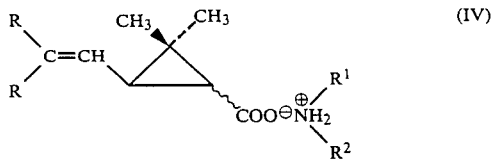

wherein R, $R^1$ and $R^2$ have the same meanings as defined above, in an aqueous or aqueous-organic solvent medium, the formation of which is promoted by adding a salt of formula (III)

wherein $R^1$ and $R^2$ have the same meanings as defined above and

X represents chloride, bromide, carbonate, sulfate, nitrate, phosphate, acetate or formiate anion and n is 1, 2 or 3.
said salt of formula (III) having buffer effect, filtering the resulting salt of formula (IV), optionally recrystallizing or mixing out, thereafter setting free the cis-cyclopropane carboxylic acid of formula (I) with an amount of a mineral or organic acid calculated corresponding to the cis isomer content or with an amount of the acid, which is less not more than 10% than the above calculated amount, in a manner known per se, or (b) adding to the sodium or potassium salt of a compound of formula (I)

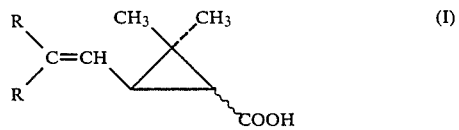

wherein R has the same meaning as defined above, a salt of formula (III), wherein $R^1$, $R^2$, X and n have the same meanings as defined above, having a buffer effect in an amount of 100 to 300 mole% in aqueous medium, filtering the resulting salt of formula (IV)

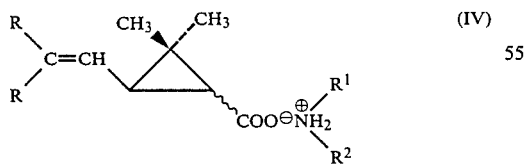

wherein R, $R^1$ and $R^2$ have the same meanings as defined above, and optionally recrystallizing thereafter setting free the cis-cyclopropane carboxylic acid or formula (I) with an amount of a mineral or organic acid calculated corresponding to the cis isomer content or with an amount of the acid, which is less not more than 10% than the above calculated amount, in a manner known per se, and isolating the trans isomer of the compounds of formula (I) by selective acidification followed by filtration.

EXAMPLE 1

In 800 ml of water containing 1.1 mole of ammonium hydroxide 1 mole of cis/trans permethrinic acid (40/60) is dissolved at 50° to 55° C. then the solution of 2 moles of ammonium acetate is 150 ml of water is added and the resulting reaction mixture is filtered off after having been cooled to 15° C. and washed with suitably cold ammonium acetate solution.

The nutsch-wet salt is dissolved in 800 ml of water of 50° to 55° C. then the pH of the solution is adjusted to 1.5 to 2 with 2N hydrochloric acid under gradual stirring and cooling. The resulting substance is filtered off, washed with water and recrystallized from 100 ml of an aqueous methanol mixture. 68 g (81.6%) of cis-permethrinic acid are obtained, m.p. 86° to 87° C.

The mother liquor of the above ammonium salt is acidified with 2.5N hydrochloric acid to pH=3.5, the resulting substance is filtered off, washed and dried. 128 g of permethrinic acid are obtained having an isomeric ratio of 10 to 15% cis/85 to 90% trans.

EXAMPLE 2

In 500 ml of water containing 1.1 mole of sodium hydroxyde 1 mole of cis/trans permethrinic acid (40/60) is dissolved at 45° to 50° C. then the solution of 2 moles of ammonium chloride in 300 ml of water is added. The resulting crystals are filtered off after having been cooled to 15° C., washed with cold ammonium chloride solution and if desired dried.

Further the process of Example 1 is followed or an other acid is used and so the separated geometrical isomers may be obtained.

Isomeric mixtures of other cyclopropane carboxylic acids may be separated in the same way.

We claim:

1. A process for separating cis and trans isomers of the Formula (I)

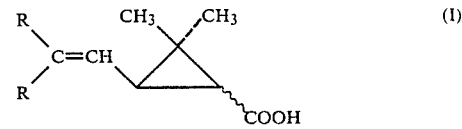

wherein
R is $C_1$ to $C_4$ alkyl or halogen, which comprises the steps of:
(a) forming a sodium or potassium salt of a mixture of cis and trans isomers of the compound of the Formula (I);
(b) treating the sodium or potassium salt comprising a mixture of cis and trans isomers of the compound of the Formula (I) at 45° to 55° C. with an aqueous solution of a salt of the Formula (III)

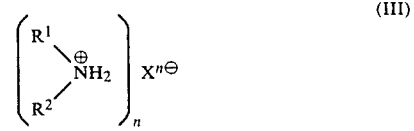

wherein $R^1$ and $R^2$ are independently hydrogen, $C_1$ to $C_5$ straight or branched chain alkyl, $C_2$ to $C_5$ straight or branched chain alkenyl, phenyl, or aralkyl having 7 to 9 carbon atoms; or $R^1$ and $R^2$ together with the adjacent nitrogen atom form a heterocyclic group containing 4 or 5 carbon atoms and which also contains an oxygen atom or an additional nitrogen atom;

X is chloride, bromide, carbonate, sulfate, nitrate, phosphate, acetate or formate; and n is 1, 2 or 3;

wherein the salt of the Formula (III) is employed in an amount of 100 to 300 mole% with respect to the sodium or potassium salt to provide a buffer effect and to obtain an aqueous solution of a salt of the Formula (IV)

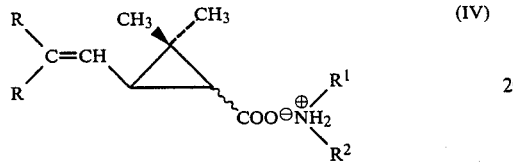

comprising a mixture of cis and trans isomers;

(c) cooling the aqueous solution of the salt of the Formula (IV) comprising cis and trans isomers to 15° C. and filtering same to obtain a precipitate of the salt of the Formula (IV);

(d) dissolving the precipitate of the salt of the Formula (IV) in water at 50° to 55° C. and adjusting the pH of the solution to 1.5 to 2 by adding an amount of a mineral or organic acid stoichiometrically corresponding to the cis isomer content of the salt down to 10% less than the stoichiometric cis isomer content of the salt thereby selectively acidifying the salt of the cis isomer of the Formula (IV) to obtain a precipitate rich in the cis isomer of the compound of the Formula (I) and a mother liquor rich in the trans isomer of the salt of the Formula (IV);

(e) separating the precipitate rich in the cis isomer of the compound of the Formula (I) from the mother liquor and recovering same; and (f) acidifying the mother liquor to obtain a precipitate rich in the trans isomer of the compound of the Formula (I).

2. The process defined in claim 1 wherein according to step (b) the salt of the Formula (III) is employed in an amount of 200 to 300 mole% with respect to the sodium or potassium salt to provide a buffer effect.

3. The process defined in claim 1 wherein according to step (b) in the salt of the Formula (III) $R^1$ and $R^2$ are each independently hydrogen, $C_1$ to $C_5$ straight or branched chain alkyl, $C_2$ to $C_5$ straight or branched chain alkenyl, phenyl or aralkyl having 7 to 9 carbon atoms.

4. The process defined in claim 1 wherein according to step (b) in the salt of the Formula (III) $R_1$ and $R_2$ are each independently hydrogen.

5. The process defined in claim 1 wherein according to step (b) the salt of the Formula (III) is selected from the group consisting of ammonium acetate and ammonium chloride.

* * * * *

UNITED STATES PATENT AND TRADEMARK OFFICE
CERTIFICATE OF CORRECTION

PATENT NO. : 4,843,174
DATED : 27 June 1989
INVENTOR(S) : Gyula BALOGH et al

It is certified that error appears in the above-identified patent and that said Letters Patent is hereby corrected as shown below: On the title page:

Item [54] Title of the Invention is to read:

--[54] PROCESS FOR SEPARATING PYRETHROID
GEOMETRIC ISOMERS --.

Item [75] Second Inventor's name is to read:
--[54] Iren Boros nee Gundar --.

Item [73] Assignee's name is to read:

-- [73] Chinoin Gyorgyszer Es Vegyeszeti Termekek
Gyara Rt. --.

Signed and Sealed this

Seventeenth Day of July, 1990

*Attest:*

HARRY F. MANBECK, JR.

*Attesting Officer*   *Commissioner of Patents and Trademarks*